United States Patent [19]
Gras et al.

[11] 4,200,725
[45] Apr. 29, 1980

[54] METHOD OF PRODUCING BLOCKED POLYISOCYANATES BY REACTION OF AN IMIDAZOLINE WITH AN ISOCYANATE

[75] Inventors: Rainer Gras, Herne; Johann Obendorf, Dorsten; Elmar Wolf, Herne, all of Fed. Rep. of Germany

[73] Assignee: Chemische Werke Huls A.G., Marl, Fed. Rep. of Germany

[21] Appl. No.: 921,091

[22] Filed: Jun. 30, 1978

[30] Foreign Application Priority Data

Jul. 1, 1977 [DE] Fed. Rep. of Germany ....... 2729704

[51] Int. Cl.² ............................................. C08G 18/80
[52] U.S. Cl. ....................................... 528/49; 528/59; 528/73; 548/349; 548/352
[58] Field of Search ................. 548/349, 352; 528/49, 528/45, 73, 59

[56] References Cited

U.S. PATENT DOCUMENTS

| | | | |
|---|---|---|---|
| 2,952,665 | 9/1960 | Bunge et al. | 528/45 |
| 3,676,402 | 7/1972 | Matsui et al. | 528/59 |
| 3,887,476 | 6/1975 | McConnell | 548/349 |
| 4,046,744 | 7/1977 | Jenkins | 528/55 |

FOREIGN PATENT DOCUMENTS

2502934 7/1976 Fed. Rep. of Germany.

*Primary Examiner*—Maurice J. Welsh
*Attorney, Agent, or Firm*—Oblon, Fisher, Spivak, McClelland & Maier

[57] ABSTRACT

This invention relates to blocked isocyanates and to a method for making blocked isocyanates by blocking the isocyanate groups of a polyisocyanate, which may be chain extended, with a cyclic amidine compound of the formula

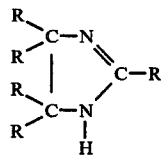

where the R's are the same or different substituents inert to isocyanate groups.

24 Claims, No Drawings

METHOD OF PRODUCING BLOCKED POLYISOCYANATES BY REACTION OF AN IMIDAZOLINE WITH AN ISOCYANATE

BACKGROUND OF THE INVENTION

1. Field of the Invention

The present invention concerns new compounds with high latent isocyanate content and to methods for producing the same.

2. Description of the Prior Art

The production of masked isocyanates, also called blocked isocyanates is known and is described in Houben-Weyl, Methoden der Organische Chemie XIV/2, pp. 61–70. Known blocking agents are tertiary alcohols, phenols, acetoacetic ester, malonic ester, acetyl acetone, phthalamide, imidazol, hydrogen chloride, hydrogen cyanide and $\epsilon$-caprolactam. In practice, the use of monophenols and $\epsilon$-caprolactam has been preferred for this purpose.

These masked isocyanates have the property of reacting like isocyanates at elevated temperatures by cleavage of the blocking groups. The more acidic the H-atom of the blocking or masking group, the easier the cleavage. Such blocked isocyanates are described in DT-OS No. 21 66 423. Also, terminally blocked isocyanates, which additionally contain uretdion groups, have been described in Dt-OS No. 25 02 934.

Blocked isocyanates are advantageous because they may be admixed with isocyanate reactable materials, such as hydroxylgroup containing polymers to form a stable mixture. When a reaction is desired, as in the production of polyurethanes from a polyisocyanate and a polyol, heat is applied to the mixture causing unblocking of the isocyanate, which permits the desired reaction to occur. Such compositions find utility as coating methods.

The most important drawback to using these blocking agents in a number of applications is the relatively high cleavage temperature, which for most phenols with aliphatic polyisocyanates, is at least 190° C. and with aromatic polyisocyanates about 30° C. lower. For this reason it has been proposed in the past to use thiophenols for which this temperature is much lower. The disadvantage of the thiophenols, however, lies in their exceedingly unpleasant odor.

It has also been proposed to admix 1–2 percent of a catalyst with the blocked isocyanate. This expedient can reduce cleavage temperatures to 125°–140° C. It has been found, however, that the introduction of such catalysts can cause the durability of the unhardened coating material to be adversely affected. The cleavage temperature of aliphatic $\epsilon$-caprolactam-blocked polyisocyanates generally lies at about 180°–190° C.

Accordingly, a need continues to exist for a blocked polyisocyanate which is characterized by the fact that the blocking group can be removed at relatively low temperatures.

OBJECTS OF THE INVENTION

It is an object of the present invention to produce blocked polyisocyanates which deblock at a temperature at least 20°–30° C. lower than the isocyanates blocked with customary blocking means.

It is a further object of the invention to produce such blocked polyisocyanates in a simple manner.

It is a still further object of the invention to produce such blocked isocyanates wherein a chain lengthening reaction is carried out after partial blocking or before blocking.

SUMMARY OF THE INVENTION

These and other objects as will hereinafter become more clear from the following discussion, have been attained by reacting a polyisocyanate with a nitrogenous cyclic amidine or imidazoline compound of the formula

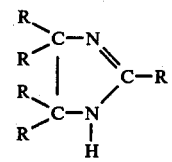

wherein the R's can be the same or different substituents inert to isocyanate groups, such as hydrogen, alkyl, cycloalkyl, alkaryl, aralkyl, aryl or heterocyclic, at a temperature of 0°–150° C., preferably 80°–120° C.

The polyisocyanates and cyclic amidines are reacted in such quantities of 0.5–1.1, and preferably 0.8–1.0 mol, of cyclic amidine to one molar equivalent of isocyanate group.

The reaction can be carried out in solvents, in the melt or even in excess polyisocyanate.

Polyisocyanates may be reacted with chain extending agents employed in less than stoichiometric amounts relative to the isocyanate groups to produce chain extended polyisocyanates which may be blocked with the cyclic amidines.

If sub-stoichiometric quantities of cyclic amidine are reacted with polyisocyanate, that is, if a ratio of less than 1 mol of amidine is reacted with one molar equivalent of isocyanate groups, the resulting reaction product will contain unreacted isocyanate groups which may be reacted with chain extending or lengthening agents reactive with isocyanate groups to obtain blocked polyisocyanates of higher molecular weight.

Blocked polyisocyanates of the following formulae are exemplary of the blocked polyisocyanates that may be produced by the method of the invention. In these formulae, R is a substituent as defined above, and R' is the bivalent organic radical of a polyol compound with two —OH groups.

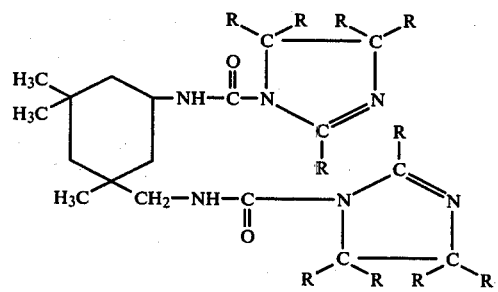

-continued

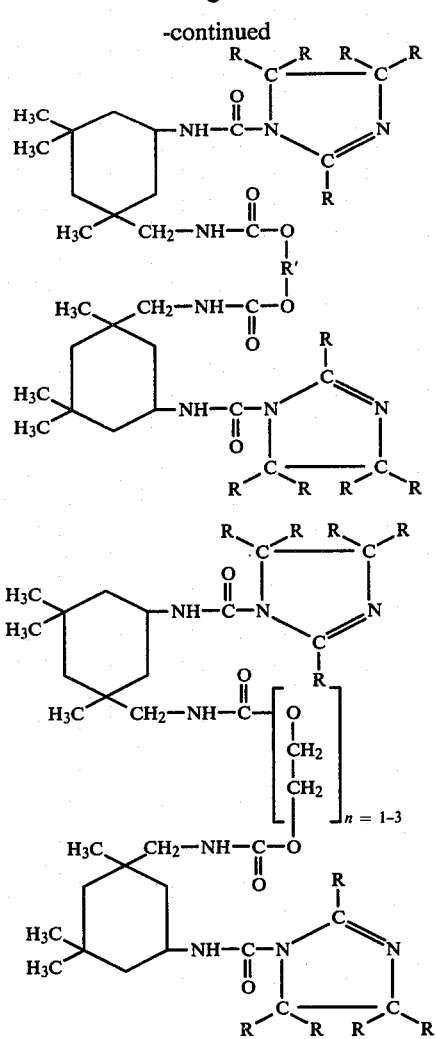

DETAILED DESCRIPTION OF THE INVENTION

Compounds suitable for blocking with cyclic amidines are, for example, polyisocyanates, in particular diisocyanates such as aliphatic, cycloaliphatic, araliphatic, aryl-substituted aliphatic and/or aromatic diisocyanates and also triisocyanates as are described, for instance, in Houben-Weyl, Methoden der Organische Chemie, Vol 14/2 pp. 61-70 and in the article by W. Siefken, Justus Liebigs Annalen der Chemie 562, pp. 75-136, like 1,2-ethylene-diisocyanate, 1,4-tetramethylene diisocyanate, 1,6-hexamethylenediisocyanate, 2,2,4- or 2,4,4-trimethyl-1,6-hexamethylenediisocyanate (TMDI) 1,12-dodecanediisocyanate, ω,ω'-diisocyanatodipropylether, cyclobutane-1,3-diisocyanate, cyclohexane-1,3- and 1,4-diisocyanate, 3-isocyanato-methyl-3,5,5-trimethylcyclohexylisocyanate, which is also called isophorondiisocyanate and abbreviated to IPDI, decahydro-8-methyl-(1,4- methanonaphthalene-2 (or 3)5-ylenedimethylene-diisocyanate, decahydro-4,7-methano-indone-1 (or 2)5 (or 6) ylenedimethylene-diisocyanate, hexahydro-4,7-methaneindone-1 (or 2)5 (or 6)ylene-diisocyanate, hexahydro-1,3- or 1,4-phenylene-diisocyanate, toluylenediisocyanate, perhydro-2,4'-and/or -4,4'-diphenylmethane-diisocyanate, ω,ω'-diisocyanato-1,4-diethylbenzene, 1,4-phenylene-diisocyanate, 4,4'-diisocyanato-diphenyl, 4,4'-diisocyanato-3,3'-dichlor-diphenyl, 4,4'-diisocyanato-3,3'-dimethoxy-diphenyl, 4,4'-diisocyanato-3,3'-dimethyl-diphenyl, 4,4'-diisocyanato-3,3'-diphenyl-diphenyl, 4,4'-diisocyanato-diphenylmethane, naphthalene-1,5-diisocyanate, toluylenediisocyanate, toluylene-2,4- or 2,6-diisocyanate, N,N'-(4,4'-dimethyl-3,3'-diisocyanato diphenyl)-uretdion, m-xylylene-diisocyanate, as well as the triisocyanates like 2,4,4'-triisocyanato-diphenylether, 4,4',4"-triisocyanato-triphenylmethane, tris-(4-isocyanato-phenyl)thiophosphate, together with any mixtures of these isomers. Other suitable isocyanates are described in the said article in the Annalen on p. 122 ff.

Particularly favored, as a rule, are the technically easily obtained aliphatic, cycloaliphatic or aromatic diisocyanates and especially 3-isocyanatomethyl-3,5,5-trimethyl-cyclohexylisocyanate (IPDI) and 2,4-toluylenediisocyanate, or isomeric mixtures thereof. The dimeric or trimeric forms of the polyisocyanates like uretdions (uretidinediones) and isocyanurates, producible by known methods, may alternatively be used.

Also suitable polyisocyanates are those which have been subjected, before the blocking with the imidazolines, to a reaction, for increasing molecular size, with so-called "chain-lengthening agents" common in isocyanate chemistry, such as water, polyols, polyamines, etc. A wide variety of bi- or trifunctional chain-lengthening agents can be used, and especially those which contain groups such as hydroxyl- and/or amino-groups, which are reactive with the isocyanate groups, can be used in such quantities that the resultant new isocyanate will have at least 2 isocyanate groups on the average. The use of water as the chain-lengthening agent produces polyisocyanates with one or more urea groupings.

Suitable polyols, which can be used include the diols and triols, e.g. ethylene glycol, propylene glycols such as 1,2- and 1,3-propanediol, 2,2-dimethylpropanediol-(1,3), butanediols like butanediol-(1,4), hexanediols such as hexanediol-(1,6),2,2,4-trimethylhexanediol-(1,6),2,4,4-trimethylhexanediol-(1,6), heptanediol-(1,7), octadecone-9,10-diol-(1,12), thiodiglycol, octadeconediol-(1,18), 2,4-dimethyl-2-propylheptanediol-(1,3), butene- or butynediol-(1,4), diethylene glycol, triethylene glycol, trans- and cis-1,4-cyclohexane dimethanol, 1,4-cyclohexanediols, glycerin, hexanetriol-(1,2,6), 1,1,1-trimethylolpropane, 1,1,1-trimethylolethane etc. Mixtures of these compounds can also be used.

Among the polyamines suitable for chain-lengthening, or increasing molecular size, are, for example, ethylenediamine-1,2, propylenediamine-1,2 and -1,3, butylenediamine-1,2, -1,3 and 1,4, as well as the hexamethylenediamines which can contain one or more $C_1$-$C_4$-radicals.

The reaction of the polyisocyanates, before blocking, with the abovementioned chain-lengthening agents in the prescribed proportions can be carried out at temperatures in the range 0°-150° C., preferably 80°-120° C.

Imidazoline derivatives of the general formula described earlier which are suitable in the sense of the present invention are, for instance, those with possibly aryl, alkyl, aralkyl, alkaryl, cycloalkyl or heterocyclic substituents. Preferably, by alkyl groups is intended to include the lower alkyl groups, i.e., those containing 1-7 carbon atoms, by aryl groups is intended to include phenyl, by cycloalkyl is intended to include 5-7 member rings, by heterocyclic is meant to include the 5–7 member rings which may include one oxygen and one or two nitrogens.

Suitable compounds include 2-methylimidazoline, 2,4-dimethylimidazoline, 2-methyl-4-(n-butyl)-imidazoline, 2-ethylimidiazoline, 2-ethyl-4-methylimidazoline, 2-benzyl-imidazoline, 2-phenyl-imidazoline, 2-phenyl-4-(N-morpholinylmethyl)-imidazoline, 2-(o-tolyl) imidazoline, 2-(p-tolyl)imidazoline, etc. Mixtures of imidazolene derivatives can also be used. This is particularly advisable if blocked isocyanates with low melting points or regions are required.

The imidazoline derivatives used in this invention can be obtained by known methods from possibly substituted vicinal diamines and aliphatic or aromatic mononitriles in the presence of elemental sulfur or sulfonyl chloride as catalyst.

The circumstances that cyclic amidines have not previously been described as blocking agents for NCO-groups, is possibly due to the fact that it could not be expected as a matter of course that the cyclic amidines would react so evenly with the NCO-groups to form urea groups, since the C=N— in the cyclic amidines might have been expected to react with the NCO-groups forming a triazine ring:

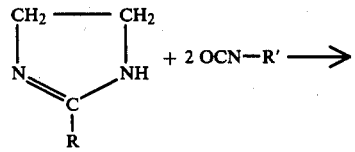

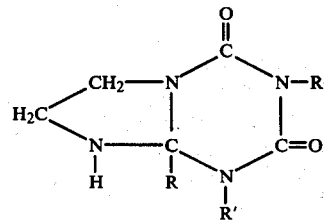

which, of course, would eliminate its utility as a blocking agent.

The blocking reaction can be carried out in solvents which are essentially non-reactive with the polyisocyanates, e.g. a ketone, such as acetone, methylethyl ketone, methylisobutyl ketone, cyclopentanone, cyclohexanone, etc.; an aromatic such as benzene, toluene, xylene, chlorobenzene, nitrobenzene, etc.; a cyclic ether such as tetrahydrofuran, dioxane, etc.; an ester such as methyl acetate, n-butyl acetate, etc.; an aliphatic chlorohydrocarbon such as chloroform, carbon tetrachloride, etc.; or an aprotonic solvent, such as dimethyl formamide, dimethyl acetamide, dimethyl sulfoxide, etc.

If the blocking agent is introduced in a proportion greater than or equal to 1 with respect to the number of isocyanate groups, the reacting mixtures are held at the specified temperatures until the NCO-content of the reacting mixture is reduced to below 0.2% NCO, or until a constant NCO-value is reached.

In a further embodiment of the present invention, a partially blocked polyisocyanate, viz. one in which the cyclic amidine has been introduced in sub-stoichiometric quantities, i.e., the ratio of cyclic amidine to isocyanate groups of less than 1:1, can be reacted with a chain-lengthening agent, of the type as described above, as means for increasing molecular size. This reaction will proceed at temperatures in the range 0°–150° C., and preferably 80°–120° C., but less than the deblocking temperature of the blocked polyisocyanate. Through this process variation, the product spectrum of the blocked polyisocyanates is extended over a wide range of practical demands. This variant is of particular interest for polyisocyanates with differently reactive NCO-groups, i.e., asymmetric polyisocyanates.

By such interchange of the adduct formation blocking sequence, blocked polyisocyanates with differing reactivity, melting point and structure can be obtained.

Compounds which are obtainable by the methods of this invention are those with molecular weights of 300–2500, preferably 300–1000. The products characteristically melt in the temperature range 30°–220° C., preferably 80°–160° C. The polyisocyanates blocked with the cyclic amidines are further characterized by a content of terminal, blocked isocyanate groups (calculated as NCO) of 4–25 wt.%, preferably 10–21 wt.%.

The compounds of the above described invention are particularly suitable, on account of their melting points combined with elevated molecular weight, as catalysts for the anionic polymerization of ε-carpolactam. The compounds can also be used in the production of wire lacquer.

Having generally described the invention, a more complete understanding can be obtained by reference to certain specific examples, which are included for purposes of illustration only and are not intended to be limiting unless otherwise specified.

EXAMPLE 1

Into a mixture of 222 parts by weight of isophorondiisocyanate (IPDI) and 300 parts of water-free acetone were slowly dripped at room temperature 292 parts of 2-phenylimidazoline dissolved in 500 parts of water-free acetone. After addition of the 2-phenylimidazoline there followed an hour of heating at 50° C. The acetone was distilled off. The last traces of acetone were removed by drying the reaction product at 60° C. in a vacuum drying chamber. The IPDI blocked with 2-phenylimidazoline is a white powder with a melting range of 98°–106° C., a glass transition temperature (DTA) of 63°–80° C. and having a cleavage temperature of about 120° C. The IR spectrum of this blocked polyisocyanate is given in FIG. 1.

Calculated: C: 70.07%; H: 7.39%; N: 16.34%; Found: C: 69.91%; H: 7.18%; N: 16.25%.

EXAMPLE 2

222 Parts by weight of IPDI were dripped into a melt of 320 parts of 2-phenyl-4-methylimidazoline in such a way that the temperature in the reaction flask did not exceed 120° C. For completion of the reaction the mixture was held at 120° C. for 3 hours. These conditions sufficed for an almost complete reaction (NCO-content of the reaction product, 0.2%). The result is a white crystalline powder with a melting range of 95°–98° C., a glass transition temperature (DTA) of 65°–85° C. and having a cleavage temperature of about 140° C. The IR spectrum of the blocked polyisocyanate is shown in FIG. 2.

Calculated: C: 70.85%; H: 7.75%; N: 15.5%; Found: C: 70.69%; H: 7.53%; N: 15.36%.

EXAMPLE 3

Into 222 parts by weight of IPDI at 80° C. 196 parts of 2,4-dimethylimidazoline were so dripped that the temperature did not exceed 90° C. After addition of all the 2,4-dimethylimidazoline, heating was continued for another hour at 100° C. The reaction product is a colorless powder with a melting range of 104°–110° C., a glass transition temperature (DTA) of 75°–90° C. and has a cleavage temperature of about 160° C. The IR spectrum of the blocked polyisocyanate is given in FIG. 3.

Calculated: C: 63.16%; H: 9.09%; N: 20.10%; Found: C: 62.98%, H: 8.91%; N: 20.21%.

EXAMPLE 4 a. 106 parts by weight of diethylene glycol were slowly and thoroughly stirred into 444 parts of IPDI at 80° C. After all the diethylene glycol was added, heating was continued for another 2 hours at 80° C. The NCO-content of the IPDI/diethylene glycol mixture then amounted to 15.1%.

b. to 556 parts by weight of the adduct formed in 4a from 2 moles of IPDI and 1 mole of diethylene glycol, 292 parts of 2-phenylimidazoline were added in small amounts at 120° C. so that the temperature did not exceed 120° C. After completion of the addition of the 2-phenylimidazoline, the reaction mixture was heated for another hour at 120° C. The reaction product is a pale yellow powder with a melting range of 100°–106° C., a glass transition temperature (DTA) of 70°–90° C. and has a cleavage temperature of about 140° C. The IR spectrum of the blocked polyisocyanate appears in FIG. 4.

EXAMPLE 5

To 556 parts by weight of the IPDI-diethylene glycol adduct described in Example 4a and at 100° C., there were added 320 parts of 2-phenyl-4-methylimidazoline in such a way that the temperature of the reaction mixture did not exceed 110° C. For completion of the reaction the mixture was heated for another 2 hours at 110° C. The reaction product is a white powder with a melting range of 95°–100° C., a glass transition temperature (DTA) of 60°–85° C. and a cleavage temperature of about 150° C. NCO could no longer be detected in the reaction product. The IR spectrum of the blocked polyisocyanate is shown in FIG. 5.

EXAMPLE 6

Into 556 parts by weight of the adduct of 2 moles of IPDI and 1 mole of diethylene glycol described in Example 4a and at 100° C., 196 parts of 2,4-dimethylimidazoline were so added by drops that the temperature did not exceed 110° C. After the addition of the 2,4-dimethylimidazoline was finished, the reaction mixture was heated for two more hours at 110° C. In the resultant product no NCO could be detected. The reaction product is a colorless substance with a melting range of 100°–107° C., a glass transition temperature (DTA) of 60°–65° C. and a cleavage temperature of about 170° C. The IR spectrum of the blocked polyisocyanate is shown in FIG. 6.

EXAMPLE 7

222 Parts by weight of IPDI was dripped into a melt of 168 parts of 2-methylimidazoline in such a way that the temperature in the reaction flask did not exceed 130° C. For completion of the reaction the mixture was held at 130° C. for 3 hours. These conditions sufficed for an almost complete reaction (NCO content of the reaction product, 0.2%). The reaction product is a white crystalline powder with a melting region of 107°–110° C., a glass transition temperature (DTA) of 82°–89° C. and a cleavage temperature of about 150° C.

EXAMPLE 8

To 556 parts by weight of the adduct of 2 moles of IPDI and 1 mole of diethylene glycol described in Example 4a and at 120° C., 168 parts of 2-methylimidazoline were added so that the temperature of the reaction mixture did not exceed 110° C. For completion of the reaction, the temperature was maintained at 110° C. for another 2 hours. The reaction product is a white powder with a melting range of 109°–112° C., a glass transition temperature (DTA) of 83°–91° C. and a cleavage temperature of 160° C.

EXAMPLE 9

Into a melt of 210 parts by weight of 2,4,4-(2,2,4)-trimethylhexamethylenediisocyanate (1:1), 292 parts of 2-phenylimidazoline were dripped in such a way that the temperature in the reaction flask did not exceed 120° C. For completion of the reaction the mixture was held at 120° C. for 3 hours. These conditions sufficed for an almost complete reaction (NCO-content of the reaction product, 0.1%). The reaction product is a white crystalline powder with a melting region of 64°–76° C., a glass transition temperature (DTA) of 57°–72° C. and has a cleavage temperature of about 140° C. The IR spectrum of the blocked polyisocyanate is given in FIG. 7.

Calculated: C: 69.32%; H: 7.57%; N: 16.73%; Found: C: 69.44%; H: 7.43%; N: 16.65%.

EXAMPLE 10

Into 210 parts by weight of 2,4,4-(2,4,4)-trimethylhexamethylenediisocyanate (1:1) at 80° C., 196 parts of 2,4-dimethylimidazoline were added by drops in such a way that the temperature did not exceed 90° C. After completion of the addition of the 2,4-dimethylimidazoline the temperature was held at 100° C. for another hour (NCO-content of the reaction product, 0.1%). The reaction product is a colorless powder with a melting region of 85°–105° C., a glass transition temperature (DTA) of 70°–91° C. and has a cleavage temperature of about 150° C. The IR spectrum of the blocked polyisocyanate appears in FIG. 8.

Calcuted: C: 72.07%; H: 9.36%; N: 20.69%; Found: C: 72.17%; H: 9.19%; N: 20.51%.

EXAMPLE 11

To a melt of 210 parts by weight of 2,4,4-(2,2,4)-trimethylhexamethylenediisocyanate (1:1), 164 parts of 2-methylimidazoline were added by drops in such a way that the temperature in the reaction flask did not exceed 130° C. For completion of the reaction, the reaction mixture was held 3 hours at 130° C. These conditions sufficed for an almost complete reaction (NCO-content of the reaction product, 0.1%). The reaction product is a white crystalline powder with a melting range of 65°–78° C., a glass transition point (DTA) of 59°–76° C. and a cleavage temperature of about 150° C.

EXAMPLE 12

To a melt of 174 parts by weight of toluylene-2,4-(2,6)-diisocyanate (80% 2,4- and 20% 2,6-) 292 parts of 2-phenylimidazoline were added in drops so that the temperature in the reaction flask did not exceed 140° C. For completion of the reaction the mixture was held at 140° C. for 3 hours. These conditions sufficed for an almost complete reaction (NCO-content of the reaction product, 0.2%). The reaction product is a white crystalline powder with a melting region of 90°–103° C., glass transition temperature (DTA) of 78°–90° C. and has a cleavage temperature of about 130° C. The IR spectrum of the blocked polyisocyanate is given in FIG. 9.

Calculated: C: 69.53%; H: 5.58%; N: 18.03%; Found: C: 69.41%; H: 5.35%; N: 18.17%.

EXAMPLE 13

To a mixture of 174 parts by weight of toluylene-2,4-(2,6)-diisocyanate (80% 2,4- and 20% 2,6-) and 300 parts of water-free acetone at room temperature were slowly added by drops 196 parts of 2,4-dimethylimidazoline dissolved in 500 parts of water-free acetone. After addition of all the 2,4-dimethylimidazoline, the temperature was kept at 50° C. for an hour. The acetone was distilled off. The last traces of acetone were removed by drying at 60° C. in the vacuum drying chamber (NCO-content of the reaction product, 0.1%). The diisocyante blocked with 2,4-dimethylimidazoline is a white powder with a melting region of 85°–105° C., a glass transition temperature (DTA) of 70°–91° C. and has a cleavage temperature of about 150° C. The IR spectrum of this blocked polyisocyanate is shown in FIG. 10.

Calculated: C: 61.62%; H: 7.03%; N: 20.70%; Found: C: 61.46%; H: 6.89%; N: 20.61%.

EXAMPLE 14

To a melt of 174 parts by weight of toluylene-2,4-(2,6)-diisocyanate (80% 2,4- and 20% 2,6-) 320 parts of 2-phenyl-4-methylimidazoline were added in drops so that the temperature in the reaction flask did not exceed 140° C. For completion of the reaction the mixture was held at 140° C. for 3 hours. These conditions sufficed for an almost complete reaction (NCO-content of the reaction product, 0.15%). The reaction product is a white crystalline powder with a melting range of 82°–99° C., a glass transition temperature (DTA) of 68°–89° C. and has a cleavage temperature of about 130° C.

EXAMPLE 15 a. To 420 parts by weight of 2,4,4- and 2,2,4-trimethylhexamethylene diisocyanate (1:1) at 80° C., 106 parts of diethylene glycol were slowly added with thorough stirring. After addition of all the diethylene glycol the mixture was kept at 80° C. for 2 hours. The NCO-content of the 2,4,4-(2,2,4)-trimethylhexamethylene diisocyanate/diethylene glycol adduct amounted then to 15.8%.

b. To 532 parts by weight of the adduct of 2 moles of 2,4,4-(2,2,4)-trimethylhexamethylene diisocyanate and 1 mole of diethylene glycol obtained in 15a and at 120° C., 292 parts of 2-phenylimidazoline were added in small amounts so that the temperature did not exceed 120° C. After completion of the addition of the 2-phenylimidazoline, the mixture was kept at 120° C. for another hour. The reaction product is a pale yellow powder with a melting region of 66°–83° C., a glass transition temperature (DTA) of 59°–75° C. and has a cleavage temperature of about 150° C.

EXAMPLE 16

To 532 parts by weight of the adduct of 2 moles of 2,4,4- and 2,2,4-trimethylhexamethylene diisocyanate and 1 mole of diethylene glycol obtained in 15a and at 120° C., 196 parts of 2,4-dimethylimidazoline were added in small amounts so that the temperature did not exceed 120° C. After addition of all the 2,4-dimethylimidazoline, the mixture was held at 120° C. for another hour. The reaction product is a pale yellow powder with a melting range of 71°–82° C., a glass transition temperature (DTA) of 61°–81° C. and has a cleavage temperature of about 170° C.

EXAMPLE 17 a. To 348 parts by weight of toluylene-2,4-(2,6)-diisocyanate (80% 2,4- and 20% 2,6-) at 80° C. 106 parts of diethylene glycol were slowly added with thorough stirring. After addition of all the diethylene glycol, the mixture was held at 80° C. for 2 hours. The NCO-content of the toluylene-2,4-(2,6)-diisocyanate/diethylene glycol mixture then amounted to 18.3%.

b. To 459 parts by weight of the adduct of 2 moles of toluylene-2,4-(2,6)-diisocyanate (80% 2,4- and 20% 2,6-) and 1 mole of diethylene glycol obtained in 17a and at 160° C. 292 parts of 2-phenylimidazoline were added in small amounts so that the temperature did not exceed 160° C. After addition of all the 2-phenylimidazoline, the mixture was heated for an hour longer at 160° C. (NCO-content of the reaction product, 0.15%). The reaction product is a pale yellow powder with a melting region of 92°–105° C., a glass transition temperature (DTA) of 79°–92° C. and has a cleavage temperature of about 140° C.

EXAMPLE 18

To 459 parts by weight of the adduct of 2 moles of toluylene-2,4-(2,6)-diisocyanate (80% 2,4- and 20% 2,6-) and 1 mole of diethylene glycol obtained in 17a and at 150° C., 196 parts of 2,4-imthylimidazoline were added in small amounts so that the temperature did not exceed 150° C. After addition of all the 2,4-dimethylimidazoline, the mixture was heated for an hour longer at 150° C. (NCO-content of the reaction product, 0.1%). The reaction product is a pale yellow powder with a melting range of 90°–107° c., a glass transition temperature (DTA) of 73°–96° C. and has a cleavage temperature of about 160° C.

EXAMPLE 19 a. To 444 parts by weight of isophorone diisocyanate at 80° C., 146 parts by weight of 2-phenyl imidazoline were added in small amounts so that the temperature did not exceed 100° C. After addition of all the 2-phenyl imidazoline, the mixture was heated for half an hour longer at 90° C. The NCO-content of the reaction product then amounted to 21%.

b. To 590 parts by weight of the reaction product obtained in 19a, and at 100° C., 106 parts by weight of diethylene glycol were added in small amounts so that the temperature did not exceed 110° C. After addition of all the diethylene glycol, the mixture was further heated as long at 100°–110° C. as the NCO-content was under 6%.

melting range: 68°–85° C.
glass transition temperature (DTA): 51°–72° C.
cleavage temperature: about 150° C.

EXAMPLE 20

General procedure for the appliance of the substances in the polymerization of ε-caprolactam 25 g (about 0,22 moles) ε-caprolactam was introduced under dry nitrogen into a clean 25×200 mm test tube.

0.6 g sodium hydride in mineral oil and 0.78 g of the blocked diisocyanate of Example 1 was added. Mixture was heated at 140°–160° C. After solidification of mixture the temperature was maintained at 160° C. for another hour. The cooled mixture was broken and cooked in boiling water for one hour to remove any remaining monomers. The yield of dried polymerisate was 70% by weight. The reduced viscosity in m-cresol (0.1 grams/100 ml) at 25° C. was 1.0.

Having now fully described the invention, it will be apparent to one of ordinary skill in the art that many changes and modifications can be made thereto without departing from the spirit or scope of the invention as set forth herein.

What is claimed as new and intended to be secured by Letters Patent of the United States is:

1. A method for producing at least a partially blocked polyisocyanate which comprises reacting a polyisocyanate with a cyclic amidine of the formula

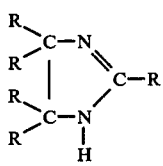

wherein each R may be the same or different substituent selected from the group consisting of hydrogen, alkyl, cycloalkyl, alkaryl, aralkyl, heterocyclic and aryl, and wherein R is inert to isocyanate groups at a temperature of 0°–150° C.

2. The method of claim 1, wherein 0.5–1.1 mole of cyclic amidine is reacted with each molar equivalent of isocyanate group.

3. The method of claim 2, wherein the cyclic amidine is added in substoichiometric quantities to the polyisocyanate to produce a partially blocked isocyanate which is then reacted with an isocyanate reactive polyvalent chain-lengthening agent at a temperature in the range of 0°–150° C., but below the deblocking temperature.

4. The method of claim 3, wherein the said reaction is carried out at a temperature in the range of 80°–120° C.

5. The method of claim 4, wherein the chain-lengthening agent is water.

6. The method of claim 4, wherein the chain-lengthening agent is a polyol.

7. The method of claim 4, wherein the chain-lengthening agent is a polyamine.

8. The method of claim 1, wherein the temperature of the reaction is 0°–150° C., and the polyisocyanate and cyclic amidine are selected so that the molecular weight of the product is 300–2500.

9. The method of claim 1, wherein the polyisocyanate with which the cyclic amidine is reacted has been produced by reacting a selected polyisocyanate with an isocyanate reactive chain lengthening agent to produce a product containing on the average two isocyanate groups per mol of product.

10. The product of the method of claim 8.

11. The product of claim 10 melting in the range of 30°–220° C. and having 4–25 wt.% NCO groups.

12. The product produced by the method of claim 1.

13. A blocked polyisocyanate of the formula

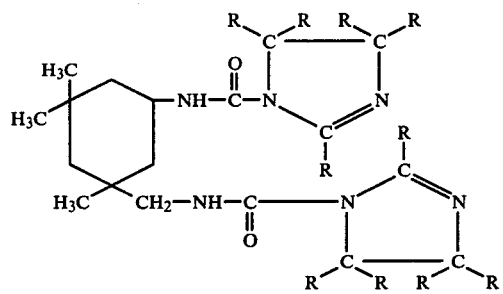

wherein each R may be the same or different substituents selected from the group consisting of hydrogen, alkyl, cycloalkyl, alkaryl, aralkyl, heterocyclic and aryl and wherein R is inert to isocyanate groups at a temperature of 0°–150° C.

14. A blocked polyisocyanate of the formula

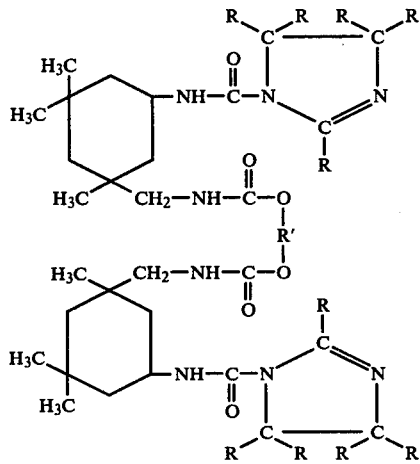

wherein R' is a bivalent organic radical of a polyol compound with two OH-groups, and wherein each R may be the same or different substituent selected from the group consisting of hydrogen, alkyl, cycloalkyl, alkaryl, aralkyl, heterocyclic and aryl and wherein R is inert to isocyanate groups at a temperature of 0°–150° C.

15. A blocked polyisocyanate of the formula

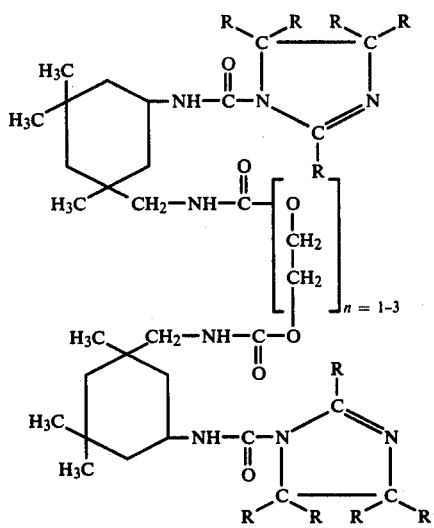

wherein each R may be the same or different substituent selected from the group consisting of hydrogen, alkyl, cycloalkyl, alkaryl, aralkyl, heterocyclic and aryl, and wherein R is inert to isocyanate groups at a temperature of 0°–150° C.

16. The product produced by the method of claim 9.
17. The method of claim 9, wherein the chain-lengthening agent is a polyol.
18. The product of the method of claim 17.
19. The method of claim 9, wherein the chain-lengthening agent is a polyamine.
20. The product of the method of claim 19.
21. The method of claim 9, wherein the chain-lengthening agent is water.
22. The product of the method of claim 21.
23. The method of claim 1 wherein R is selected from the group consisting of hydrogen, $C_1$–$C_7$ alkyl, $C_5$–$C_7$ cycloalkyl, 5 to 7-membered heterocyclic rings which may include one oxygen and one or two nitrogen atoms, phenol, $C_1$-alkyl substituted phenol, and benzyl.
24. The polyisocyanate of any of claims 13, 14 or 15 wherein R is selected from the group consisting of hydrogen, $C_1$–$C_7$ alkyl, $C_5$–$C_7$ cycloalkyl, 5 to 7-membered heterocyclic rings which may include one oxygen and one or two nitrogens, phenol, $C_1$-alkyl-substituted phenol, and benzyl.

* * * * *